United States Patent [19]

Casselberry et al.

[11] Patent Number: 4,686,848

[45] Date of Patent: Aug. 18, 1987

[54] HIGH TEMPERATURE PARTICULATE FILTER MEDIA TEST UNIT

[75] Inventors: Robert F. Casselberry, Pittsburgh; Robert C. Kania, Gibsonia, both of Pa.

[73] Assignee: Umec Corporation, Latrobe, Pa.

[21] Appl. No.: 673,379

[22] Filed: Nov. 20, 1984

[51] Int. Cl.⁴ .............................................. G01N 1/24
[52] U.S. Cl. .................................... 73/38; 73/863.12; 73/863.23
[58] Field of Search ................. 73/38, 863.23, 863.12, 73/28; 55/267, 270

[56] References Cited

U.S. PATENT DOCUMENTS

| | | | |
|---|---|---|---|
| 3,517,557 | 6/1970 | Granger et al. | 73/863.12 |
| 3,784,902 | 1/1974 | Huber | 73/863.23 X |
| 3,841,145 | 10/1974 | Boubel | 73/28 |
| 3,881,359 | 5/1975 | Culbertson | 73/863.12 |
| 3,903,745 | 9/1975 | Bolser | 73/863.23 X |
| 3,965,748 | 6/1976 | Boubel et al. | 73/863.23 X |
| 3,986,386 | 10/1976 | Beltzer et al. | 73/863.12 |
| 4,154,088 | 5/1979 | Werner | 73/863.12 X |
| 4,342,234 | 8/1982 | Bernath | 73/863.12 |

Primary Examiner—Jerry W. Myracle
Assistant Examiner—Joseph W. Roskos
Attorney, Agent, or Firm—Reed Smith Shaw & McClay

[57] ABSTRACT

A portable test device for evaluating the effectiveness of different filtering media, preferably metallic filtering media, in removing particulates from the gas stream of an exhaust stack at temperatures between about 300° F. and about 1500° F., including a probe member insertable directly into the gas stream of the exhaust stack and a particulate filtering facility in which the metallic filtering media to be tested are positioned. Facilities are provided for the isokinetic sampling and passing of the sample stream withdrawn by the probe member from the probe member to and through the particulate filtering facility while maintaining the temperature thereof substantially at the temperature it had within the exhaust stack. Facilities are also provided which permit the metallic filtering media to be readily replaced by different metallic filtering media to permit comparisons of filtering effectiveness. Also included are downstream particulate removal means which remove all particulates not earlier filtered by the metallic filtering media, to permit the total particulate content of the gas stream to be analyzed.

12 Claims, 4 Drawing Figures

HIGH TEMPERATURE PARTICULATE FILTER MEDIA TEST UNIT

FIELD OF THE INVENTION

The invention relates generally to devices for evaluating high temperature particulate filtering media to assist designers of industrial emission control equipment.

DISCUSSION OF THE TECHNICAL PROBLEM

Conventional emission control equipment for industrial facilities often include baghouse structures which use a high number of large fabric "bags" at a low air-to-cloth ratio to remove particulate matter from a gaseous stream. A large number of variables affect the choice of media selected for use as a baghouse bag, including among others the temperature of the gas stream, velocity of the gas stream at the collection point, shape, size, and chemical makeup of the particulates in the gas stream, total grain loading of particulates in the gas stream, and cleanability of the media. Through years of trial and error, it is now reasonably predictable which conventional fabric media will perform suitably in a particular gas stream, once the characteristics of the gas stream are known.

Devices known as particulate sampling trains are used to sample a gas stream in an industrial stack to determine the particulate content thereof, by filtering the sampled gas through a glass fiber filter media at a temperature above the condensation temperature of water to remove particulates, and thereafter through impingers at lower temperatures to remove chemical and water content from the sampled gas. Equipment of this type is commerically available, e.g., from Anderson of Atlanta, Ga., and is useful in EPA Sampling Method 5. However, such equipment has not found use in evaluating the effectiveness of different commercially interesting filtering media, perhaps because the volumetric flow rates and filtering temperatures found in such equipment does not correspond meaningfully to the volumetric flow rates and filtering temperatures in commercial baghouses. The glass fiber filter media commonly used in such sampling equipment is useful at high temperatures but is not commercially feasible because it is fragile and does not survive conventional cleaning operations.

Recently, it has been suggested that metallic filtering media may prove useful in constructing high temperature air filtration systems. See, for example, U.S. Pat. No. 3,948,623 to Ostby et al. Metallic filtering media may have great potential in producing a commercial-sized air filtration system which can act upon higher temperature gas streams (and thereby be positioned much more near the source thereof) without the danger of fire or explosion which presently exists in conventional baghouses. However, short of constructing a full-scale operational high-temperature system and testing various full-sized high temperature metallic filtering media in use, there has heretofore been no known facility for determining the optimum high temperature filtering media for a particular application.

It is of particular importance that filtering media evaluation be conducted at the high temperatures at which commerical use is contemplated, because the filtering characteristics will be likely to be affected by elevated temperatures; e.g., the metallic filtering media may "open up", or the particulates may change from tacky or greasy to dry, depending upon temperature. In addition, it is important that filtering media be tested at volumetric flow rates similar to those of contemplated use, in order that durability, type of weave, blinding characteristics adn cleanability may be meaningfully evaluated.

It would be desirable to have a device which could evaluate the filtering characteristics of various high temperature filtering media in the environment in which actual use would occur, to enable the designer to select an optimum media configuration for each application. It would be a further advantage if such a device could simultaneously serve to identify for the designer the particulate content and character of the gas stream.

SUMMARY OF THE INVENTION

A portable, high temperature particulate filter media test unit provides information to a designer of emission control systems concerning the relative performance of a variety of different high temperature filtering media, at the temperature range and in the air-to-filter media-ratio at which the emission control system is contemplated for commerical use. In particular, information relating to filtering efficiency, durability, and cleanability of selected high temperature filtering media under commercial operating conditions is provided. In addition, the test unit of the present invention provides substantial information concerning the particular, chemical and moisture composition of the gas stream which is to be treated.

The device includes a probe member insertable into the high temperature gas stream which can isokinetically withdraw a continual, representative sample stream therefrom, gas sample transfer means for transferring the sample stream from the probe while maintaining the temperature thereof at the sampling temperature, and a particulate filtering means including selected high temperature filtering media for evaluation which are held in the path of the sample stream to filter particulate materials therefrom. The particulate filtering means includes temperature control elements which maintain the sample stream and the selected filtering media at the sampling temperature, so that filtering evaluation can occur at operating temperatures contemplated for a commercial emission control system. The particulate filtering means also includes access means for permitting filtering media to be conveniently replaced with other filtering media, to provide comparative data. Preferably, the particulate filtering means also includes flow rate control means to control the air-to-filtering media-ratio of the selected filtering media, to adapt it to within the range contemplated for a commercial emission control system.

DESCRIPTION OF THE PREFERRED EMBODIMENTS

Figure 1:
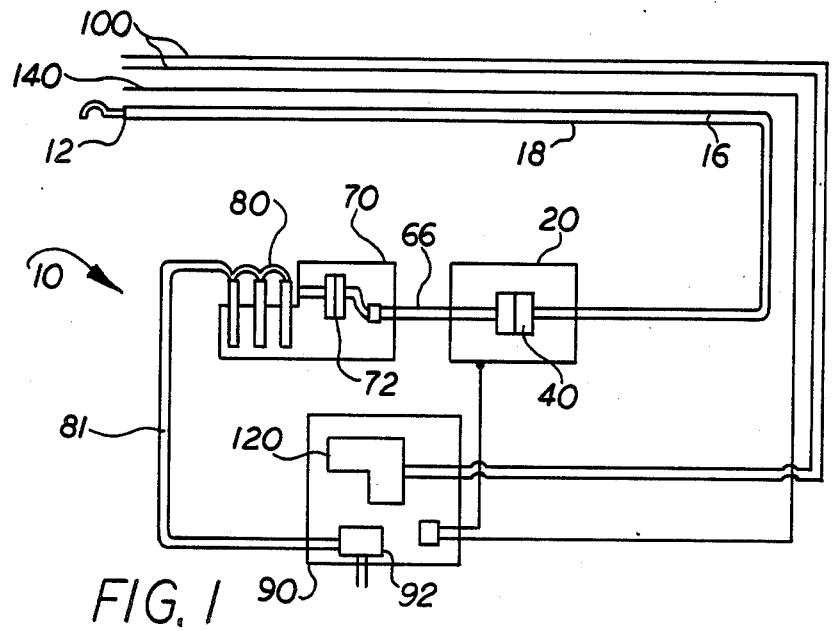
FIG. 1 is a schematic view of a preferred embodiment of the high temperature particulate filtering media test unit of the present invention.

With reference to FIG. 1, there is shown a high temperature particulate filtering media test unit 10, including as major elements an elongated isokinetic sampling probe member 12, elongated sampling line 16, high temperature particulate filter assembly 20, secondary particulate filter assembly 70, glass impinger assembly 80, meter control box 90, pitot tubes 100, manometer 120, and temperature sensor 140.

Probe member 12 is adapted for insertion into the exhaust gas flow of a wide variety of industrial facilities to extract a steady, isokinetic sample stream therefrom. While the preferred precise configuration of probe member 12 is shown, it does not limit the present invention, as other suitable units are commercially available such as from Anderson of Atlanta, Ga. Of course, because the present invention is particularly beneficial in high temperature applications, it is important to utilize a probe member 12 which can function at temperatures up to about 1500° F.

Elongated sampling line 16 is preferably a flexible conduit suitable for transferring the sample stream from probe member 12 while maintaining the temperature substantially constant at the high temperatures at which it was sampled, e.g., from 300° F. up to about 1500° F. To this end it is preferred that sampling line 16 include heating and insulating sheath 18 therearound. Although not limiting the invention, sheath 18 in a preferred embodiment may be formed of Fiberfrax Braid having electrical heating wires extending therethrough.

Figure 2:
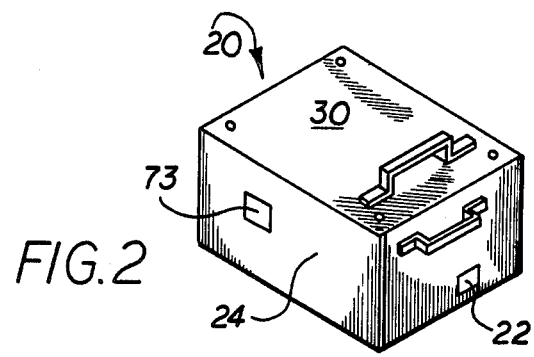
FIG. 2 is a view of the particulate filter assembly of the high temperature particulate filtering media test unit.
Figure 3:
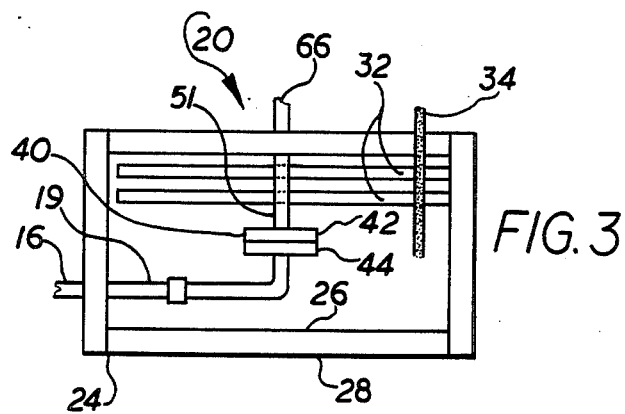
FIG. 3 is a plan view of the particulate filter assembly of the high temperature particulate filtering media test unit with lid portions removed for clairty.

With reference also to FIGS. 2 and 3, sampling line 16 transfers the sample stream into high temperature particulate filter assembly 20 through a conduit 19 which extends through an orifice 22 in insulated housing 24. Housing 24 is a high temperature box-like structure which is preferably constructed of stainless steel and covered on its inside and outside surfaces with substantial layers of insulating materials 26 and 28 respectively. Typically these layers 26 and 28 are 2 inches thick and, are composed of industrial insulation. Housing 24 preferably includes a lid member 30 which is likewise insulated and which is conveniently detachable to provide ready access into housing 24 for the purpose of changing the filtering media to be evaluated. In the preferred embodiment, housing 24 has the dimensions of nineteen inches by twelve inches by twelve inches.

Mounted within housing 24 is a heating facility 32, preferably taking the form of a pair of parallel elongated electrical strip heaters. In the preferred embodiment, the heating facility consists of two, sixteen and three-quarter inch long inconel strip heaters. While the precise form of heating facility 32 does not limit the invention, it should have adequate capacity, in cooperation with insulating layers 26 and 28, to maintain the temperature inside housing 24 at the same level as the temperature of the gas stream in the exhaust stack being sampled; e.g., 300° F. up to about 1500° F.

A thermocouple 34, typically of the K type, is positioned within housing 24 to monitor the temperature therein and provide a signal which can be compared to a signal generated by a temperature sensor 140 which is positioned in the exhaust stack being sampled, for purposes of controlling heating facility 32.

Figure 4:
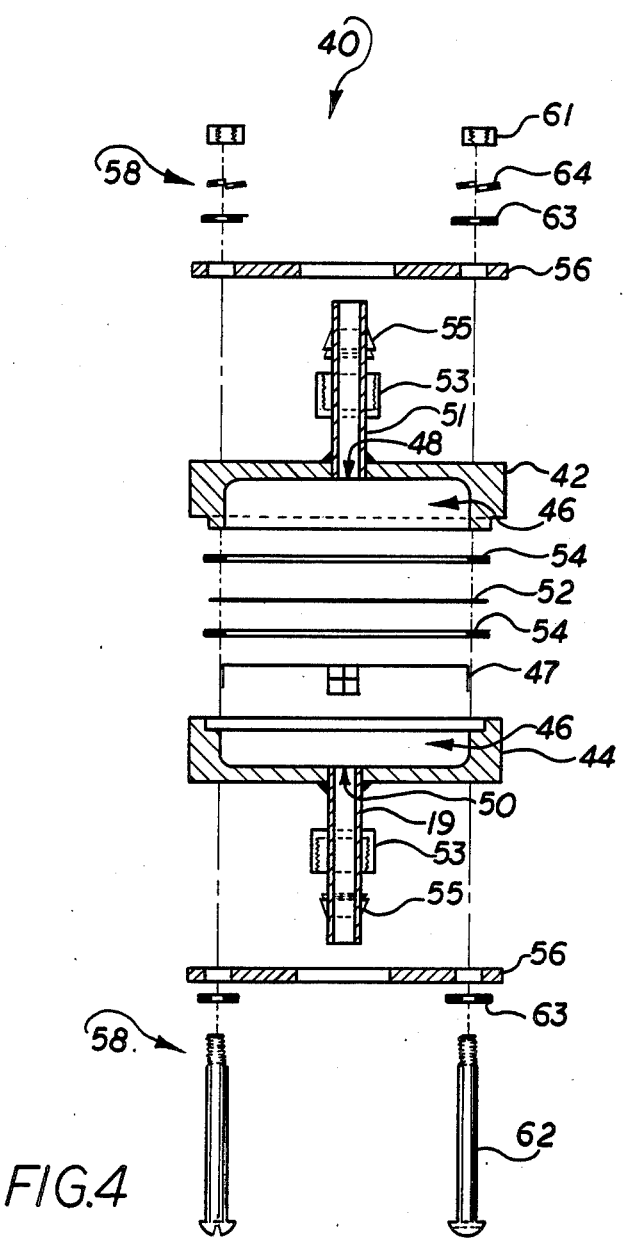
FIG. 4 is an exploded view of the holder of the particulate filter assembly unit shown in FIG. 1 or FIG. 3.

Also mounted in housing 24 is a high temperature filtering media holder 40 through which the sample stream is passed from conduit 19. As best shown in FIG. 4, holder 40 includes opposing halves 42 and 44 which when secured together as intended form a disc-shaped chamber 46 therebetween into which the sample stream may enter from conduit 19 through orifice 48 and exit through orifice 50 into conduit 51. Typically filter holder 40 is four inches in diameter. Nut 53 and ferrule 55 ensure that there is an airtight seal between conduits 19 and 51 and opposing halves 42 and 44. Within intermediate chamber 46 there is mounted on filter support 47 a metallic filtering media 52 which is to be evaluated, filtering media 52 being sealingly retained in desired position by a pair of gasket members 54 which are biased thereto on either peripheral edge of filtering media 52.

Although not limiting to the invention, halves 42 and 44 may be held together by a pair of rigid plates 56 secured on either side by nut and bolts assemblies 58 containing nuts 61, bolts 62, washers 63 and lock washers 64. Of course, numerous alternative fastening facilities can be used without departing from the intention of the invention.

The sample stream passes out of filter assembly 20 through orifice 73 and downstream through tube 66 into secondary particulate filter assembly 70, wherein substantially all remaining particulates are removed from the sample stream. Filter assembly 70 may conveniently take the form commonly used in the art of EPA Sampling Method 5, i.e., a glass fiber filtering media 72 maintained at a temperature above the condensation point of water. Of course, after the sample stream departs filter assembly 20 at the elevated temperature of the exhaust stack, it may be desireable to cool it before introducing it to filter assembely 70. Tube 66 can be used to cool the gas before it enters filter assembly 70.

After departing assembly 70, the sample stream may be passed through glass impinger assembly 80 in which substantially all water content and selected chemical components may be removed for analysis. Glass impinger assembly 80 is known in the art and requires no further description herein. A glass impinger assembly 80 useful in the practice of the present invention may be obtained from Anderson of Atlanta, Ga., as Model #217.

The sample stream is advanced downstream from glass impinger assembly 80 through tube 81 to the meter control box 90, where the volume of the sample stream is determined after particulates, water and selected chemical contents have been removed and the temperature has been lowered to about ambient.

Meter control box 90 also includes a vacuum pump 92 which serves to advance the sample stream through the system at a desired rate, and a manometer 120 which measures and indicates gas velocity. Connected to manometer 120 is a pair of S-type pitot tubes 100, the ends of which are inserted with probe member 12 into the exhaust stack to measure the velocity of the gas stream in the exhaust stack. Vacuum pump 92 is then controlled such that the sample stream is drawn into probe member 12 at the same rate as the gas stream is advancing in the exhaust stack so that isokinetic sampling is effected. Isokinetic sampling is important in order to ensure that the particulate content of the sample stream corresponds with the particulate content of the gas stream in the exhaust stack. Thus the flow rate in probe member 12 is largely determined by the flow rate of the gas stream in the exhaust stack.

For the purposes of the present invention it is desirable that the evaluation of selected high temperature filtering media take place not only at substantially the same temperature but also substantially the same air-to-filtering media-ratio as the commercial use which is ultimately contemplated. Particularly, the preferred embodiment is directed to the evaluation of selected metallic filtering media. In this manner, valuable information can be obtained concerning plugging, blinding, cake and cleaning of the selected filtering media. For this purpose, and with reference to FIG. 4, chamber 46 is dimensioned so that the sample stream undergoes a predetermined reduction in flow rate upon entry therein, to a level which corresponds to the desired range of air-to-filtering media-ratio through filtering media 52 while still maintaining an isokinetic sampling rate. The present invention is particularly adapted for evaluation of high temperature metallic filtering media which because of their substantial strength can generally be utilized at much higher air-to-filtering media-ratios (15:1 to 23:1) than conventional fabric filtering media (3:1 to 5:1). It is possible to construct test unit 10 using a relatively small sample of the filtering media to be evaluated, e.g., 4 inch diameter sample, while still maintaining the air-to-filtering media-ratio within the desired operational range. Through this approach, a readily portable test unit 10 can be provided which can be easily moved to a test site and used by a single operator.

To provide the desired air-to-filtering media-ratio in the preferred embodiment of the invention, sampling line 16 and conduit 19 are formed with an inside diameter of about three-eights inch, which then opens into disc-shaped chamber 46, which has an inner diameter of about four inches.

In operation, test unit 10 is transported to the industrial location where particulate testing is desired and probe member 12 and pitot tubes 100 are inserted into a sampling orifice of the exhaust stack of the facility. A first selected filtering media 52 is utilized within housing 24 for a preselected time period, e.g., thirty minutes, afterwhich the first filtering media would be removed and a second selected filtering media would be tested for the same time period. After a suitable number of different filtering medis were tested, the particulate laden media could be returned to a suitable analytical facility for analysis and evaluation of the relative performances of each of the tested filtering media. The filtering media will be analyzed for total mass of particulate collected, size of particulate collected, cleanability of the filtiering media with the specific particulate collected, expected length of time before cleaning becomes necessary, and durability of the filtering media with the specific particulate and air-to-filtering mediaratio under investigation. The collected particulate itself will preferably be analyzed to determine its characteristics, e.g., whether it is dry, sticky, granular, fluid, volatile, electrically conductive, etc.

The particulate content of the glass fiber filtering media of filter assembly 70 would also preferably be analyzed to determine the total particulate content of the gas stream within the stack and to determine the absolute filtering efficiency of the high temperature filtering media being tested. Indeed, in one application of the invention it may be desirable to replace the glass fiber filtering media with each replacement of the metallic filtering media being tested. In the preferred embodiment, the high temperature filtering media being tested is metallic, preferrably made from stainless steel inconel, brass or aluminum although it is evident that the media can be made from any metal.

In addition, the content of glass impinger assembly 80 is preferably analyzed in a manner known in the art, so that a comprehensive picture of the particulate, chemical and water content of the gas stream will be available to the system designer.

Through a single or series of such evaluation procedures it is possible to economically and reliably gather sufficient information about the preferred high-temperature filtering media and each specific gas stream for which an emission control system is to be provided, to permit a system designer to select the optimum filtering media for use in a high temperature 'baghouse' which has substantial advantages over the conventional, fabric-filled baghouses currently in use.

While a presently preferred embodiment of the invention has been shown and described, it may be otherwise embodied within the scope of the appended claims.

We claim:

1. A device for evaluating the effectiveness of selected metallic high temperature filtering media using a gas stream from the same exhaust stack and at a temperature at which said filtering media will be commercially used, comprising:

a probe member insertable into said gas stream to withdraw a gas sample therefrom, said gas stream having an established temperature between about 300° F. and about 1500° F. and containing a quantity of particulates therein;

a gas sample transfer means connected at one end to said probe member for transferring said gas sample from said probe member, said gas sample transfer means including a temperature control means for maintaining said gas sample substantially at said established temperature;

a particulate filtering means connected to said gas sample transfer means to receive said gas sample and filter portions of said quantity of particulates therefrom; said particulate filtering means including selected metallic high temperature filtering media to be evaluated, a means for holding said selected metallic high temperature filtering media in the path of said gas sample, means for maintaining said gas stream and said selected metallic high temperature filtering media substantially at said established temperature, and an access means for permitting said selected metallic high temperature filtering media to be conveniently replaced with other selected metallic high temperature filtering media within said holding means to permit a comparison of the effectiveness of different selected metallic high temperature filtering media; and a first means for measuring said established temperature within said exhaust stack, and wherein said temperature control means comprises a second means for measuring the temperature within said particulate filtering means, and a heating means for controlling the temperature within said particulate filtering means in response to the signal from said first and second measuring means.

2. The device as set forth in claim 1, further comprising a flow rate control means for controlling the volumetric flow rate of said gas sample through said selected metallic filtering media to be evaluated, to adapt said volumetric flow rate to within the range at which said selected metallic filtering media will be commercially used.

3. The device as set forth in claim 2, wherein said flow rate control means comprises a gas sample pump means, a means for measuring the velocity of gas stream in said exhaust stack, and a means for controlling said gas sample pump means to substantially match the velocity of said gas sample in said probe member with the velocity of said gas stream in said exhaust stack.

4. The device as set forth in claim 3, wherein said flow rate control means further comprises a chamber means in which said selected metallic filtering media is retained, wherein said chamber means is dimensioned to control the air-to-filtering media-ratio within said chamber means within a range between 15:1 and 23:1.

5. A device for evaluating the effectiveness of selected high temperature filtering media using a gas stream from the same exhaust stack and at a temperature at which said filtering media will be commercially used, comprising:
a probe member insertable into said gas stream to withdraw a gas sample therefrom, said gas stream having an established temperature between about 300° F. and about 1500° F. and containing a quantity of particulates therein;
a gas sample transfer means connected at one end to said probe member for transferring said gas sample from said probe member, said gas sample transfer means including a temperature control means for maintaining said gas sample substantially at said established temperature;
a particulate filtering means connected to said gas sample transfer means to receive said gas sample and filter portions of said quantity of particulates therefrom; said particulate filtering means including selected high temperature filtering media to be evaluated, a means for holding said selected high temperature filtering media in the path of said gas sample, means for maintaining said gas stream and said selected high temperature filtering media substantially at said established temperature, and an access means for permitting said selected high temperature filtering media to be conveniently replaced with other selected high temperature filtering media within said holding means to permit a comparison of the effectiveness of different selected high temperature filtering media;
a second particulate filtering means for removing additional particulates from said gas stream located downstream of said particulate filtering means; and
an impinger means located downstream of said second particulate filtering means for removing additional components from said gas stream;
whereby the composition of said gas stream within said exhaust stack can be determined by analysis of the components removed from said gas sample by said particulate filtering means, said second particulate filtering means and said impinger means.

6. The device as set forth in claim 5, wherein said selected high temperature filtering media is metallic, substantially formed of a material selected from the group consisting of stainless steel, inconel, brass or aluminum, 7. The device as set forth in claim 6, wherein said material is formed as a flat weave, a twilled weave or a dutch-twilled weave.

8. A method for evaluating the effectiveness of selected high temperature filtering media by sampling the particulate content of a gas stream in an exhaust stack, comprising the steps of:
withdrawing a sample stream from said gas stream in said exhaust stack, said gas stream having an established temperature between about 300° F. and about 1500° F. and containing a quantity of particulates therein;
moving said sample stream from said exhaust stack to a particulate filter means while maintaining the temperature of said sample stream substantially at said established temperature;
moving said sample stream through a first high temperature filtering media in said particulate filter means for a predetermined time period while maintaining the temperature of said sample stream substantially at said established temperature, to filter out a first measurable portion of said quantity of particulates from said sample stream at said established temperature;
replacing said first high temperature filtering media with a second and different high temperature filtering media;
moving said sample stream through said second and different high temperature filtering media for a second predetermined time period while maintaining the temperature of said sample stream at said established temperature to filter out a second measurable portion of said quantity of particulates;
comparing said first measurable portion to said second measurable portion to evaluate the relative effectiveness of said first and second high temperature filtering media;
moving said sample stream from said particulate filter means to a downstream particulate removal means, said downstream particulate removal means removing substantially all of the remainder of said quantity of particulates from said sample stream at temperature differing from said established temperature; and
analyzing the particulates in said particulate filter means and said downstream particulate removal means to determine the particulate content of said gas stream in said exhaust stack.

9. The method as set forth in claim 8, further comprising the step of:
controlling the volumetric flow rate of said sample through said first and second high temperature filtering media within a range at which said first and second filtering media will be commercially used.

10. The method as set forth in claim 9, wherein said range of volumetric flow rate, measured by air-to-filtering media-ratio, is between 15:1 and 23:1.

11. The method as set forth in claim 10, wherein said withdrawing step is practiced at an isokinetic rate relative to the velocity of said gas stream in said exhaust stack.

12. The method as set forth in claim 11, further comprising the step of cleaning said first and second portion from said first and second high temperature filtering media, respectively, in a predetermined manner to evaluate the relative cleanability of said filtering media.

* * * * *

UNITED STATES PATENT AND TRADEMARK OFFICE
CERTIFICATE OF CORRECTION

PATENT NO.  :  4,686,848

DATED       :  August 18, 1987

INVENTOR(S) :  Casselberry et al.

It is certified that error appears in the above-identified patent and that said Letters Patent is hereby corrected as shown below:

Column 2, line 5:   delete --adn-- and substitute therefor --and--.

Column 2, line 29:  delete --particular-- and substitute therefor --particulate--.

Column 5, line 43:  delete --medis-- and substitute therefor --media--.

Column 5, line 52:  delete --mediaratio-- and substitute therefor --media-ratio--.

Column 8, line 40:  delete --temperature-- and substitute therefor --temperatures--.

Signed and Sealed this

Sixteenth Day of August, 1988

*Attest:*

DONALD J. QUIGG

*Attesting Officer*     *Commissioner of Patents and Trademarks*